United States Patent [19]
Johnson

[11] Patent Number: 5,358,470
[45] Date of Patent: Oct. 25, 1994

[54] SHOULDER IMMOBILIZATION RESTRAINT

[76] Inventor: James Johnson, 1702 S. University Ave., P.O. Box 6001, Fargo, N. Dak. 58108

[21] Appl. No.: 51,394
[22] Filed: Apr. 23, 1993
[51] Int. Cl.⁵ ............................................. A61F 5/04
[52] U.S. Cl. ......................................... 602/20; 602/4; 602/62; 126/DIG. 19; 126/DIG. 15
[58] Field of Search ............... 602/4, 5, 20, 12, 62, 602/64; 126/DIG. 15, DIG. 19; 2/44, 45

[56] References Cited

U.S. PATENT DOCUMENTS

| | | | |
|---|---|---|---|
| 3,515,131 | 6/1970 | Stevens | 602/20 |
| 3,554,190 | 1/1971 | Kaplan | 2/44 X |
| 3,780,729 | 12/1973 | Garnett | 602/4 |
| 4,480,637 | 11/1984 | Florek | 602/4 |
| 5,095,894 | 3/1992 | Marble | 602/4 X |

FOREIGN PATENT DOCUMENTS

2181952  5/1967  United Kingdom .................. 602/20

Primary Examiner—Richard J. Apley
Assistant Examiner—Beverly A. Meindl
Attorney, Agent, or Firm—Douglas L. Tschida

[57] ABSTRACT

An assembly and method for restricting shoulder and upper arm motion and supporting a wrist to facilitate healing of the clavicle. The assembly includes a length adjustable, elastic belt or abdominal harness and from which an elastic shoulder strap and support pad are adjustably trained about an injured shoulder. VELCRO fasteners selectively restrain the support pad to the shoulder strap and the shoulder strap and a wrist support to the belt.

13 Claims, 7 Drawing Sheets

SHOULDER IMMOBILIZATION RESTRAINT

BACKGROUND OF THE INVENTION

The present invention relates to fracture restraint devices and, in particular, to an assembly for adjustably immobilizing a shoulder to facilitate healing, for example, of a fractured clavicle, while supporting the wrist of the affected extremity.

Traditional medical practice for treating a fractured clavicle is to support the clavicle and adjoining muscles and tissue in a stable predetermined alignment to the torso to prevent misalignment of the bone through arm and wrist motion during the healing purpose. A variety of strap and splint assemblies have been developed for this purpose. Each attempts to immobilize the affected limb to assure proper healing with minimal pain.

Some of such assemblies comprise preferred wrapping arrangements of elastic bandages. Some comprise preconfigured harnesses which mount to the upper torso and include padded straps. A variety of known slings, straps, splints and bandages are described in a book entitled *Fractures in Children*, Rockwood, Jr. et al., p. 865 (Lippincott Co. 3rd ed., 1991). These assemblies include support straps which encircle one or both shoulders. Crossing straps and underarm supports are also disclosed. Some of the assemblies include straps which immobilize the affected shoulder in relation to the other shoulder and upper body or to an underarm support. Alternative bandage assemblies completely immobilize the affected shoulder and adjacent arm via wraps which encircle the arm and chest or which encircle the shoulder and chest in a figure-of-eight wrapping arrangement.

A padded shoulder harness, known as a MEEK clavicle brace is disclosed in U.S. Pat. No. 3,141,456. This assembly provides straps which encircle each shoulder and are joined together with a vertical coupling strap behind the neck.

In preference to the known art, a system is desired which selectively restrains the affected extremity and simultaneously supports the adjacent wrist. The assembly should provide as wide a range of adjustment as possible and preferably accommodate both children and adults. The assembly should also be capable of being installed by other than a physician and provide a durable and washable construction.

SUMMARY OF THE INVENTION

It is accordingly a primary object of the present invention to provide an adjustable, restraint and shoulder support assembly which finds particular advantage for the treatment of injuries to the clavicle.

It is a further object of the invention to provide an assembly which selectively supports the wrist.

It is a further object of the invention to provide an assembly which accommodates a variety of support pads and permits selective placement of the pads to the assembly and affected extremity.

It is a further object of the invention to provide an assembly which includes elastomer straps which flex and provide a directable and variable support tension, depending upon selected anchoring points established along a length adjustable abdominal harness or belt.

Various of the foregoing objects, advantages and distinctions of the invention are obtained in a presently preferred construction which comprises a belt, an over-the-shoulder support strap, a clavicle support pad and a wrist support and all of which mount in adjustable relation to each other. The shoulder strap and wrist support fasten to the belt. The shoulder strap and harness are each constructed of an elastic material. The belt, shoulder strap, and wrist support each include regions covered with a VELCRO fastener material, whereby the relative length of the belt and shoulder strap can be adjusted and the corresponding restraint forces can be directionally applied with varying degrees of tension or immobilizing support to the affected shoulder. The support pad and wrist support can also be adjusted.

A support pad retainer is securable along the shoulder strap. The retainer comprises an elastic strap which loops about and may be positioned along the shoulder strap. A support pad of preferred shape mounts to the retainer. Cushioned pads having alternative surface configurations to accommodate differing types of support and immobilization are disclosed. All components are washable and the assembly can be worn beneath or above normal clothing.

Still other objects, advantages and distinctions of the invention will become more apparent upon reference to the following detailed description with respect to the appended drawings. To the extent various modifications or improvements have been considered, they are described as appropriate. The following description should not be strictly construed in limitation of the scope of the invention. Rather, the invention should be interpreted within the scope of the further appended claims.

DESCRIPTION OF THE PREFERRED EMBODIMENT

Figure 1:
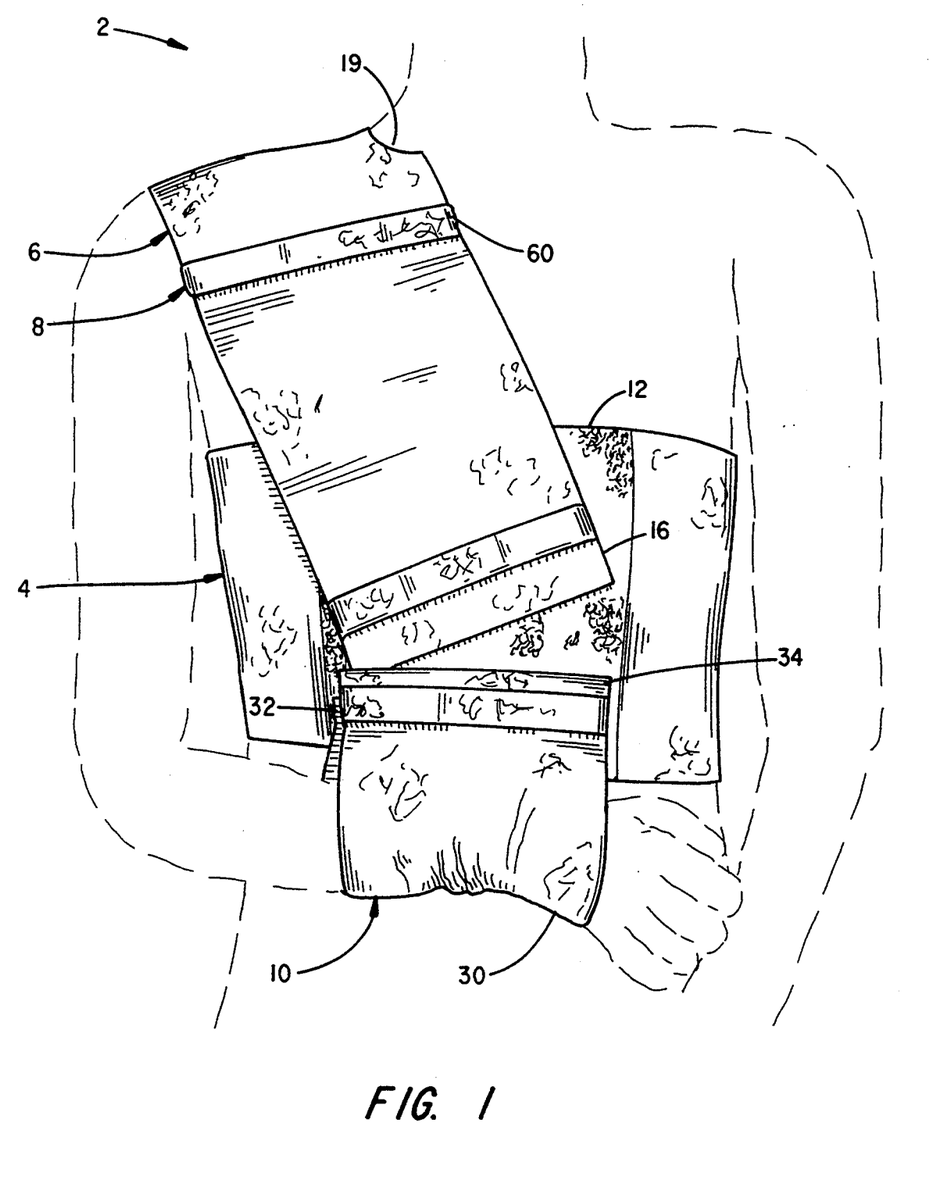
FIG. 1 is a front elevation drawing of the clavicle and wrist restraint assembly of the invention shown in mounted relation to the human torso, which is shown in phantom line.
Figure 2:
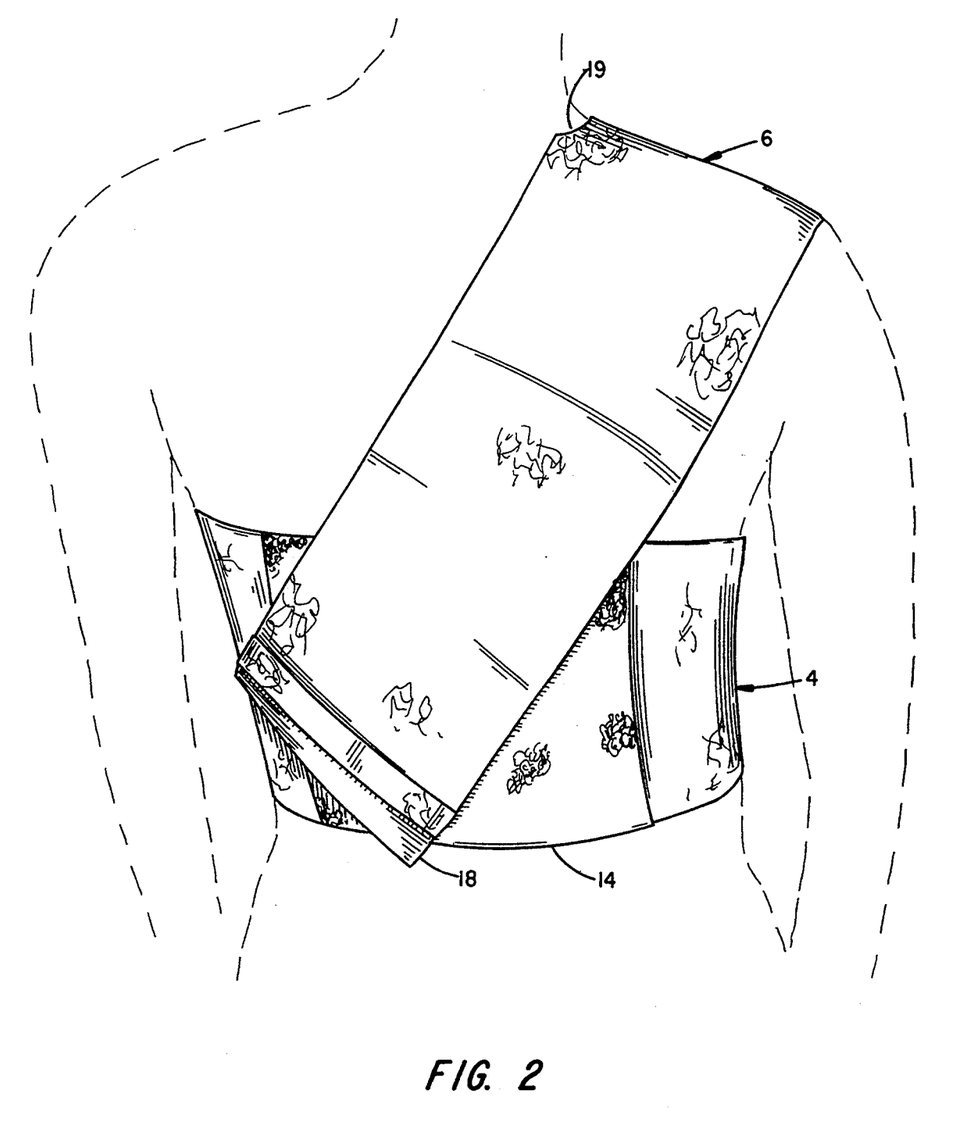
FIG. 2 is a rear elevation drawing of the restraint of FIG. 1 as typically mounted.

FIGS. 1 and 2 depict front and rear elevation views of the improved shoulder or clavicle support assembly 2 of the invention, as typically worn by a convalescent who is shown in phantom line. The assembly 2 generally includes a length adjustable abdominal harness or belt 4, an over-the-shoulder strap 6, a support pad, retainer assembly 8 and a wrist support 10. A number of regions of VELCRO fastener material 12 and 14 are provided at the anterior and posterior surfaces of the harness 4. The regions 12, 14 mate with mating fastener portions 16 and 18 secured to the ends and inner surfaces of the shoulder strap 6. The members, sizes and shapes of the regions 12, 14 and 16, 18 can be varied as desired along the harness 4 and strap 6.

The fastener regions 12, 14 permit an adjustment of the angular orientation of the strap 6 relative to the affected shoulder and the localized area of the injury. Once the strap 6 is properly oriented with respect to the injury, the retainer assembly 8 is manipulated along the strap 6 to position a conformal pad 15, 36 or 38, reference FIGS. 3, 5 and 6, to support the clavicle. The configuration of the pad is shaped to conform and provide preferential support to the specific injury, whether a fracture of the clavicle or rupture or tearing of the ligaments or adjoining muscles, and to facilitate healing.

The shoulder strap 6 is constructed of an elastic webbing. The width is sized to approximate the neck-to-arm shoulder space of most individuals and thereby encompass substantially the entire length of the clavicle. Typical web widths of 2 to 8 inches accommodate most children and adults. Multiple webs may also be sewn together along longitudinal edges to provide wider widths. A cutout 19 may be provided at the neck to prevent chaffing.

The length of the strap 6 and the length, positioning and number of regions of the VELCRO fastener material 12, 14 and 16, 18 are established to provide a wide variety of angular orientations of the strap 6 along the anterior and posterior surfaces of the torso, as the strap 6 is stretched over the shoulder. The resultant forces applied to restrain the pad retainer assembly 8 to the torso and the support applied to the clavicle or adjoining ligaments may thereby be controlled. In its presently preferred form, the strap 6 includes elastomer fibers which accommodate longitudinal and lateral stretching of the webbing.

Strips of VELCRO fasteners 16 and 18 are secured to the ends of the strap 6. Upon securing the fasteners 16, 18 to the mating fastener regions 12, 14 of the harness, the pressure applied to retain the retainer pad assembly 8 is determined. Although fastener regions 16 and 18 are presently provided only at the extreme ends of the strap 6, additional regions may be provided along the length of the strap 6 and whereby the length of the stretched portion of the strap 6 can be controlled. Still other regions 21 may be provided on the exposed surface of the strap 6 to mate with an overlapping strap 6 or possibly the wrist support 10, reference FIG. 7.

Figure 3:
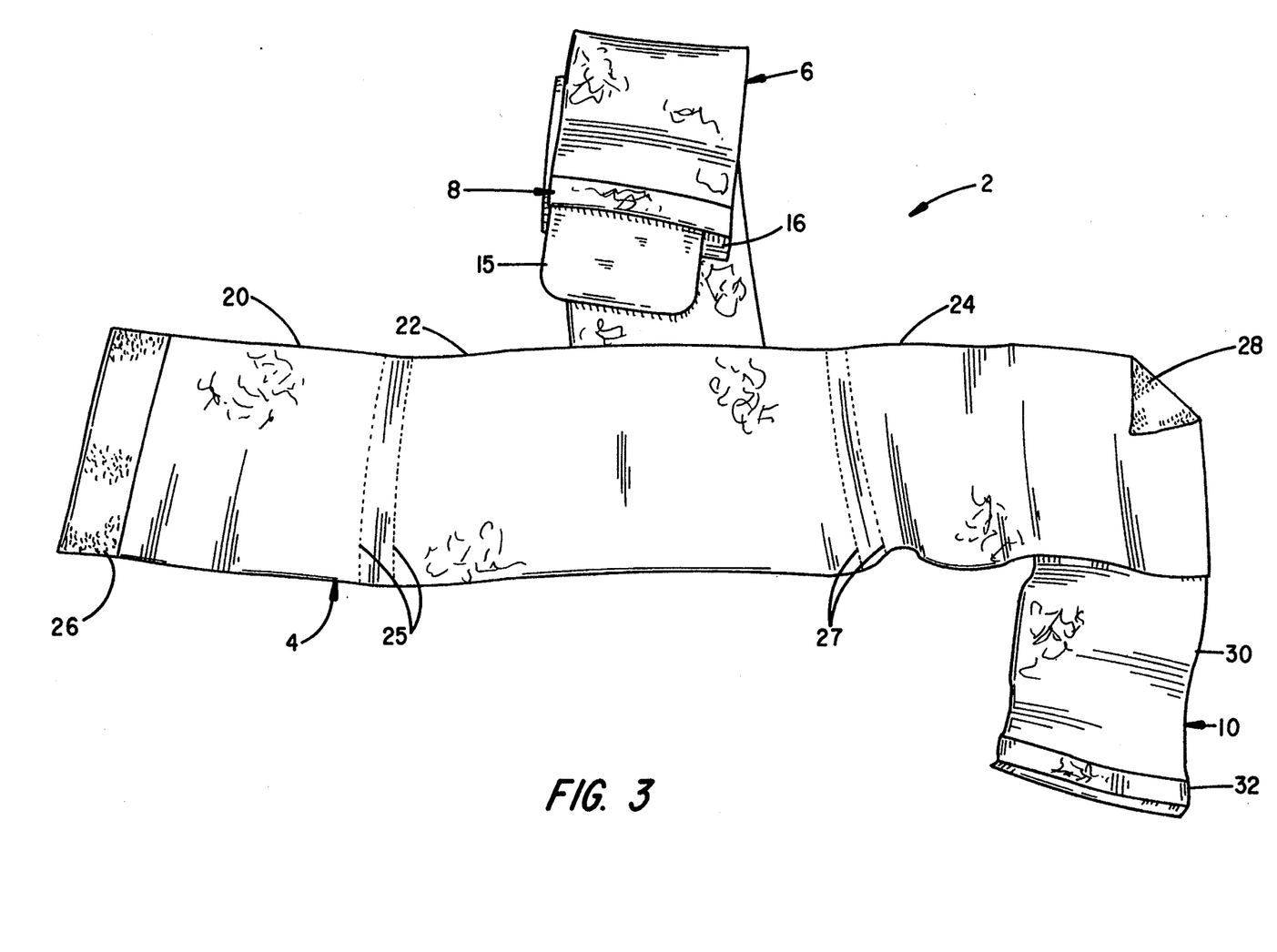
FIG. 3 is a drawing shown in exploded view of the restraint assembly.

With attention to FIG. 3, the belt or abdominal harness 4 can be constructed as a single panel of webbing material, a series of vertical panels 20, 22, 24 or a series of horizontal panels (not shown), which are stitched to one another along adjacent edges. Presently, vertically arranged webbing panels 20, 22, 24 are stitched to form a belt which accommodates the shape of the upper torso and which evenly distributes the compressive retention forces over the surface area of the harness 4. Fatigue, chaffing, circulatory restriction etc. are thereby minimized, once the harness 4 is secured to the torso.

Darts at stitching 25, 27 determine the ultimate shape of the harness 4. The width of the belt 4 preferably extends from the waist or top of the hips to approximately the center of the chest or solar plexus. Widths in the range of 2 to 8 inches will accommodate most individuals.

Secured to overlapped ends of the belt 4 are mating regions of VELCRO fastener material 26, 28 and whereby the length of the belt 4 is appropriately sized to the convalescent. Multiple bands of VELCRO fastener material 26, 28 can be stitched to the ends of the belt 4 to permit a range of length adjustment to the waist size of the convalescent. The established length should be sized in relation to the forces exerted by the strap 6, which tend to pull on the belt 4. The amount of pulling force depends on the positioning of the mating fastener regions 12, 14 of the shoulder strap and to the regions 16, 18 of the shoulder strap 6 of the belt 4.

The use of bands of VELCRO fastener material 12, 14, 16, 18, 26 and 28 is preferred in lieu of multiple buckle or mechanical fasteners, since a wider and more flexible range of adjustment is obtained at each of the belt 4, shoulder strap 6, pad retainer assembly 8, and wrist support 10. The fastener material and each component of the assembly are also washable and provide a durable long-lifed support system.

Figure 4:
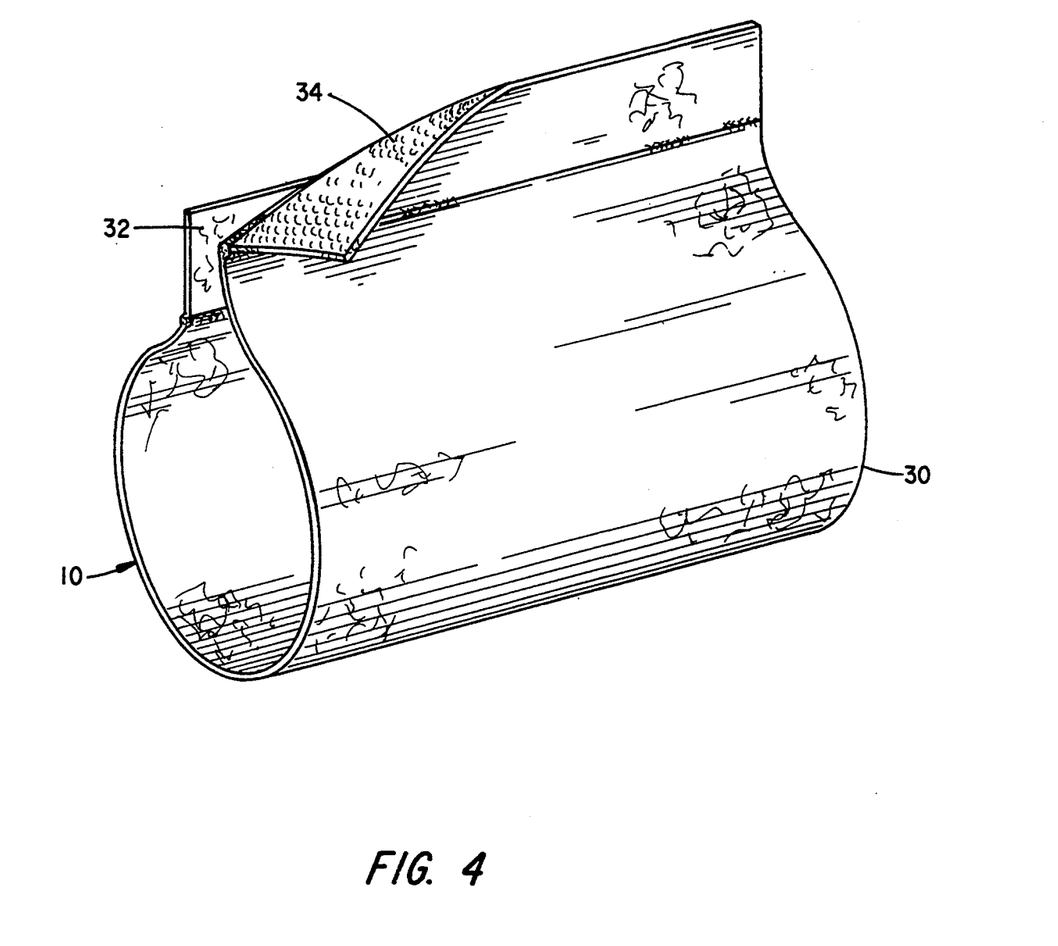
FIG. 4 is a perspective drawing of the wrist restraint.

With continuing attention to FIG. 1 and also to FIG. 4, a detailed perspective drawing is shown of the wrist support 10. Preferably the wrist is supported to minimize motion of the arm and thereby minimize transmitted forces across the injured area, such as extension of the clavicle, and resulting pain as the injury heals. The support comprises a length of elastic fabric webbing 30. Strips of VELCRO fastener material 32, 34 are secured to the edges of the webbing 30 to form a cylindrical support which wraps about the wrist and forearm. A portion of the fastener 34 mates with the fastener region 12 at the belt 4 to retain the wrist support 10 to the belt 4 and allow the wrist and arm to be supported from the belt 4. The wrist support 10 may also be secured to the strap 6 at a fastener region 21, reference FIG. 7. The relative height and mounting relationship of the arm is thereby adjustable with wide latitude. Prior supports either fail to support the wrist or bind the wrist in a series of wraps or require a separate sling.

The webbing width and resultant length of the wrist support 10 may be varied as desired. Preferably the webbing 30 includes elastomer fibers to provide a slight degree of stretch. The ability of the wrist support 10 to stretch minimizes possible release of the fastener material 34 from the belt 4 with normal body movement. In a similar fashion each of the belt 4 and strap 6 are able to expand and contract with body motion, while maintaining the injured limb in a preferred therapeutic orientation.

Due to the wide range of adjustability obtained with the belt 4 and strap 6, the assembly 2 can be worn over an undergarment. Under certain circumstances, the assembly 2 can be worn over outer clothing. A greater degree of freedom is thereby provided to the convalescent which does not restrict most lifestyle activities. This freedom also increases the probability the convalescent will not prematurely discontinue use of the support assembly 2.

Figure 5:
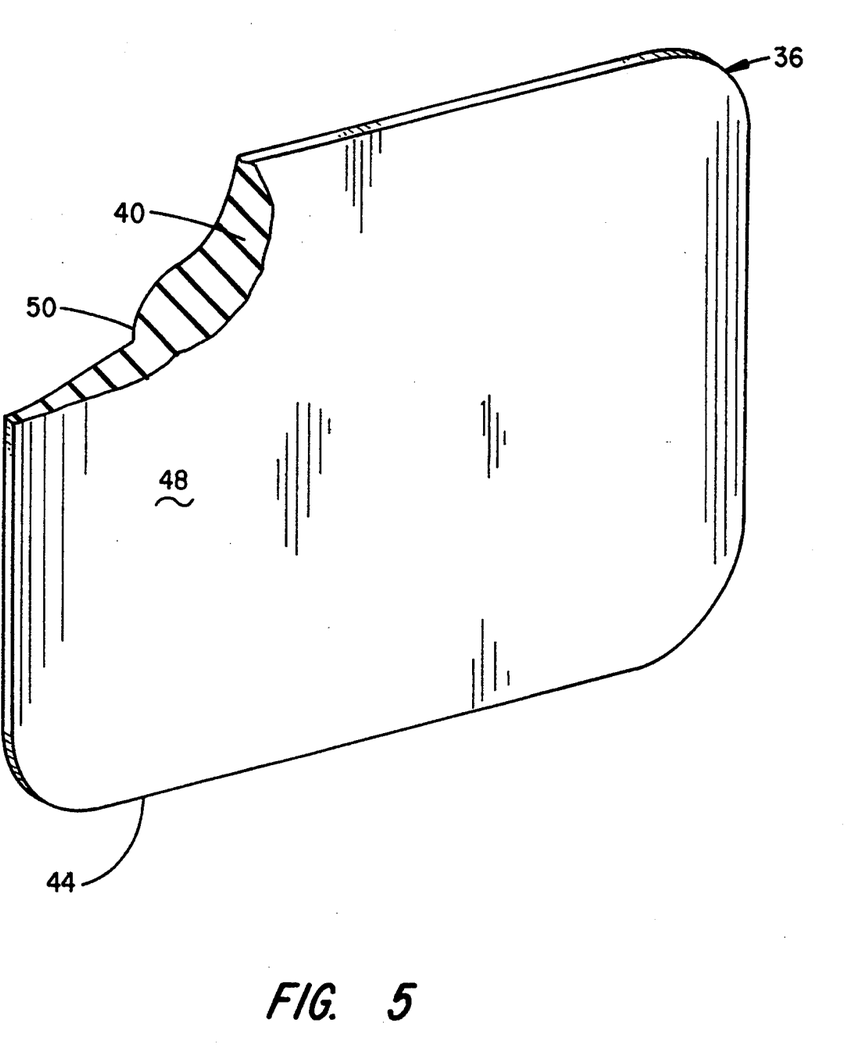
FIG. 5 is a perspective drawing, shown in partial cutaway of one support pad.
Figure 6:
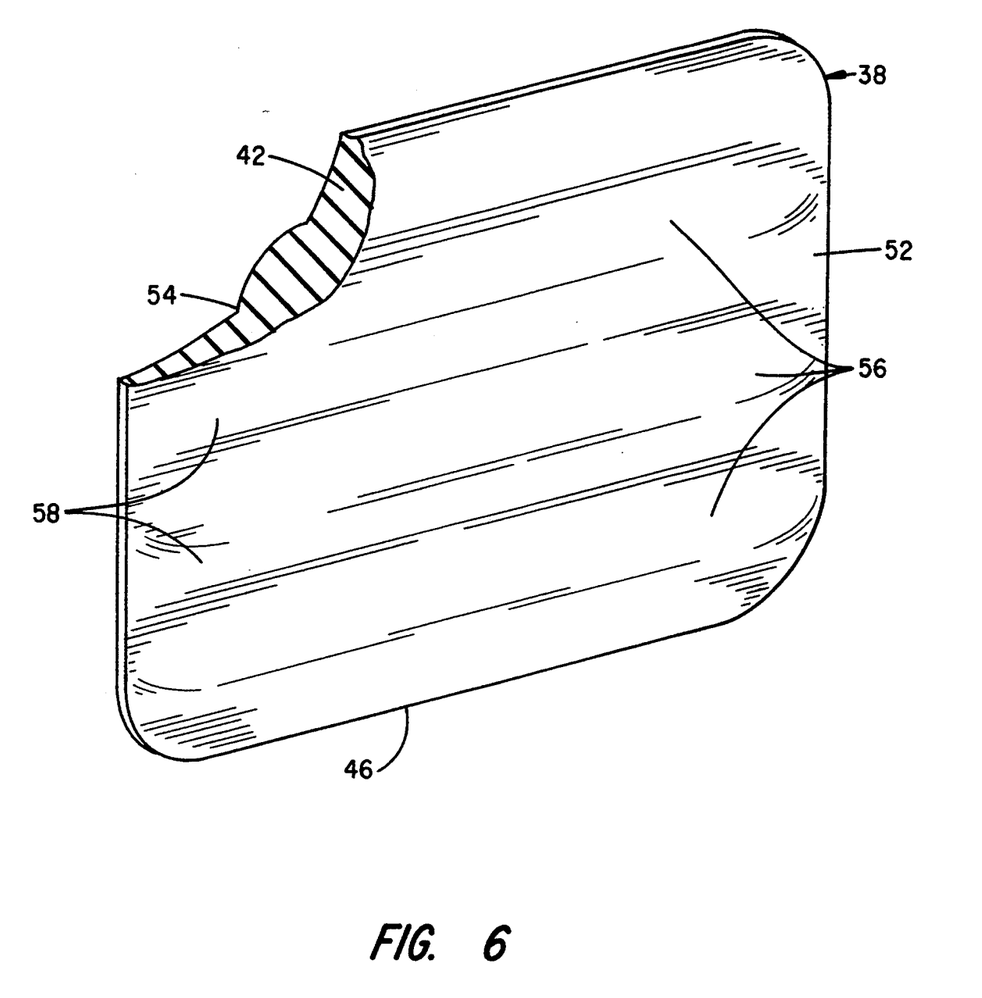
FIG. 6 is a perspective drawing shown in partial cutaway of an alternative clavicle support pad.

With further attention directed to FIGS. 5 and 6, alternative clavicle support pads 36 and 38 are shown which may be used in conjunction with the strap 6. Each pad is formed of a sculptured foam material, and is shaped to a generally rectangular configuration. Other materials such as neoprene, cotton padding or any material that is soft, conforms and supports the injury may also be used to advantage. The center portion of each pad 36, 38 provides a relatively thicker region 40, 42 than the outer peripheral edges 44, 46. The front and rear surfaces 48, 50 of the pad 36 are substantially flat. In contrast, the surfaces 52, 54 of the pad 38 provide a series of adjacent longitudinal ridges 56 and valleys 58. It is to be appreciated other geometries and surface configurations may be substituted to accommodate the particular injury being treated.

Depending upon the injury, the type of pad that contacts the injured extremity can be appropriately positioned to enhance the support. That is, longitudinal fractures may be better supported with the pad 38. Well defined breaks may be better supported with the pad 36.

Returning attention to FIG. 1, each pad is secured to the shoulder strap 6 via a retainer assembly 8. An elastic strap 60 is particularly bonded to each pad 15, 36 or 38 to form a loop of a width approximating the width of the shoulder strap 6. The specific pad can thereby be adjusted along the strap 6 to properly position and retain the support pad in relation to the injury. Multiple pads may also be secured as necessary along the strap 6 and to contact anterior and posterior surfaces of the torso during treatment.

Figure 7:
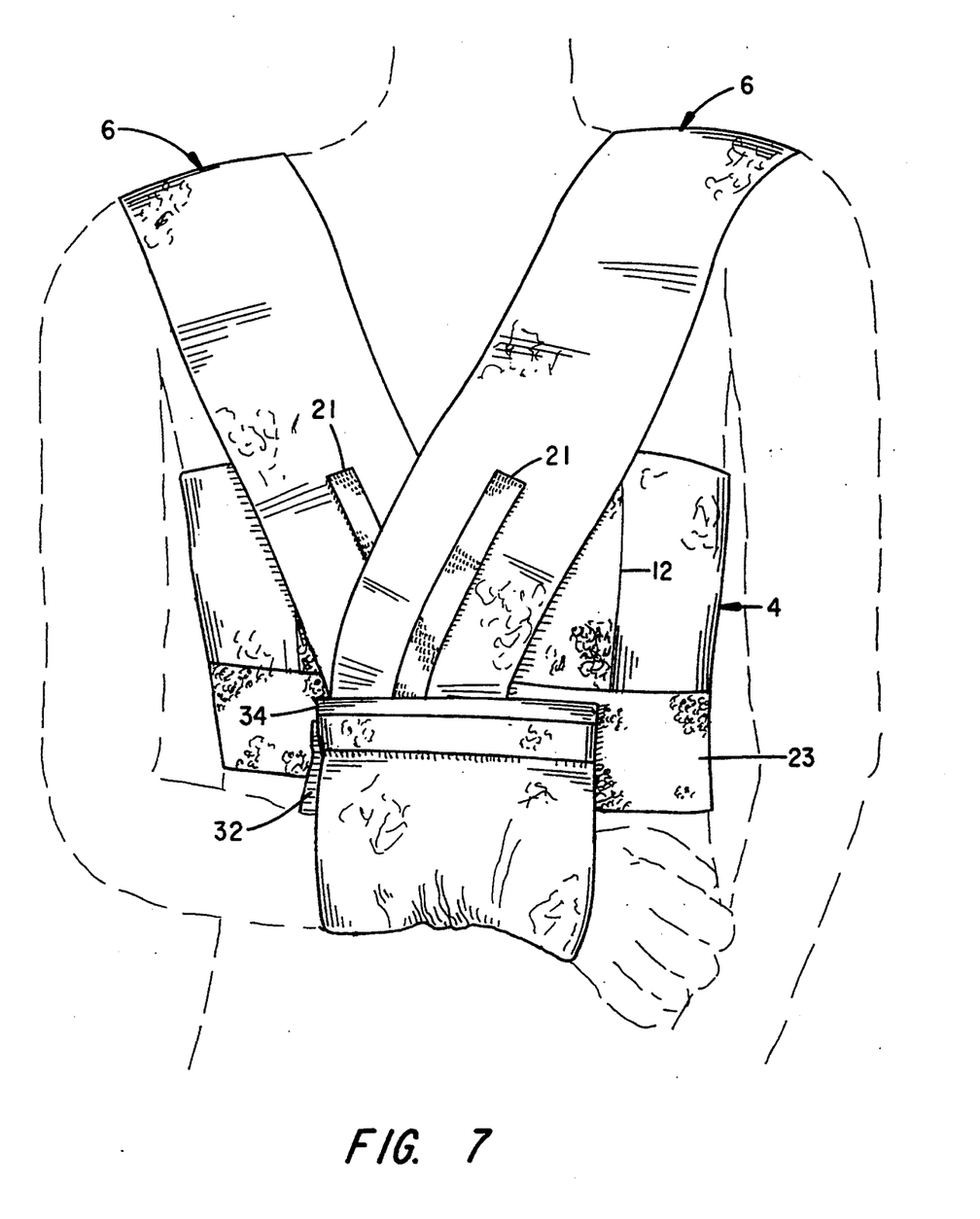
FIG. 7 is a front elevation drawing of the clavicle and wrist restraint assembly of the invention and including a pair of straps to support both shoulders of a convalescent.

Although a single shoulder strap 6 has been depicted, it is to be understood that other strap arrangements can be provided. For example, pairs of separate straps 6 can be trained in a crisscrossing arrangement about each shoulder to the belt 4, such as shown in FIG. 7. Alternatively, a suspenders-like mounting can be obtained by vertically training each strap from the belt 4 over each shoulder. In either instance, each shoulder is separately supported.

While the invention has been described with respect to its presently preferred construction and considered modifications and improvements, it is to be appreciated still other constructions may be suggested to those skilled in the art. Accordingly, the following claims should be interpreted to include all of those equivalent embodiments within the spirit and scope of the described invention.

What is claimed is:

1. Shoulder support apparatus comprising:
   (a) harness means for mounting about the abdomen of a convalescent and having a belt, wherein said belt comprises a continuous web of elastic material, wherein said belt includes a plurality of fastener regions of hook and loop fastener material secured to front and rear surfaces of said belt, wherein a selected one of said fastener regions secured to the rear surface mounts to a selected one of said fastener regions at the front surface to establish the tension and length of said belt about the abdomen;
   (b) a continuous elastic strap including a plurality of regions of hook and loop fastener material mounted to front and rear surfaces of said strap, wherein said strap comprises a web of a width substantially spanning the length of the convalescent's clavicle, wherein at least a selected one of said fastener regions at each end of said strap on said rear surface mounts to a selected one of said fastener regions on the front surface of said belt, and whereby upon training said strap over a shoulder of the convalescent the tension of said strap may be varied;
   (c) a conformal support pad; and
   (d) means for retaining said pad along said strap in contact with a selected region of the torso.

2. Apparatus as set forth in claim 1 wherein said belt is comprised of a plurality of panels of elastic webbing, and wherein said panels are stitched to one another along adjacent peripheral edges.

3. Apparatus as set forth in claim 1 wherein said belt is comprised of a plurality of panels of elastic webbing and wherein said panels are sewn to one another to provide a uniform tension at all regions of the belt upon mounting said belt to the abdomen.

4. Apparatus as set forth in claim 1 including means for supporting the wrist of the convalescent comprising a web band including means for securing the band about the wrist and further including a fastener region of hook and loop fastener material and wherein said fastener region mounts to a selected one of the fastener regions at the front surface of said belt or said strap.

5. Apparatus as set forth in claim 1 wherein said pad includes a plurality of raised projections, which projections extend from a portion of said pad and mount to contact and conform to the torso.

6. Apparatus as set forth in claim 1 wherein said support pad includes a looped retainer which mounts about said strap and whereby said pad is selectively securable along said strap.

7. Apparatus as set forth in claim 1 including:
   (a) a second pad;
   (b) a continuous elastic second strap including a plurality of regions of hook and loop fastener material mounted to front and rear surfaces of said second strap, wherein said second strap comprises a web of a width substantially spanning the length of the convalescent's clavicle, wherein a selected one of said fastener regions at each end of said strap on the rear surface strap mounts to a selected one of said fastener regions on the front surface of said belt and whereby upon training said second strap over a second shoulder of the convalescent the tension of said strap may be varied; and
   (d) means for retaining said second pad along said second strap in contact with a selected region of the torso.

8. Apparatus as set forth in claim 4 wherein said band includes regions of said hook and loop fastener material, wherein a selected pair of said regions mount together to secure the band about the wrist.

9. Shoulder support apparatus comprising:
   (a) harness means for mounting about the torso of a convalescent and having a belt, wherein said belt includes a plurality of fastener regions of first and second mating fasteners, wherein ones of said fasteners are secured to front and back surfaces of said belt, and wherein a selected pair of said fastener regions mount to one another to establish the length and tension of said belt about the torso;
   (b) first and second elastic straps, wherein each strap includes a plurality fastener regions of said first and second mating fasteners mounted to front and rear surfaces of said strap, wherein at least a selected one of said fastener regions at each of said first and second straps mounts to a selected one of said fastener regions at said belt, and whereby upon training each of said first and second straps over separate shoulders of the convalescent the tension of said first and second straps may be varied; and
   (c) means having a support pad for retaining said pad along said strap in contact with a selected region of the torso.

10. Shoulder support apparatus comprising:
   (a) harness means for mounting about the abdomen of a convalescent and having a belt, wherein said belt comprises a continuous web of elastic material, wherein said belt includes a plurality of fastener regions of hook and loop fastener material secured to front and rear surfaces of said belt, wherein at least a selected one of said fastener regions secured to the rear surface mounts to a selected one of said fastener regions at the front surface to establish the tension and length of said belt about the abdomen;

(b) a continuous elastic strap including a plurality of regions of hook and loop fastener material mounted to front and rear surfaces of said strap, wherein at least a selected one of said fastener regions at one end of said strap mounts to a selected one of said fastener regions on said belt, and whereby upon training said strap over a shoulder of the convalescent the tension of said strap may be varied;

(c) a conformal support pad; and (d) means for retaining said pad along said strap in contact with a selected region of the torso.

11. A method for treating an injured shoulder comprising:

(a) securing an elastic belt about the abdomen of a convalescent to establish the length and tension of said belt about the abdomen, wherein said belt includes a plurality of regions of mating hook and loop fastener material secured to front and rear surfaces of said belt;

(b) training a continuous elastic strap having a plurality of regions of said hook and loop fastener material secured to front and rear surfaces of said strap over a shoulder of the convalescent and selectively retaining a selected one of said fastener regions of said strap to a selected one of said regions at said belt to establish the tension of said strap about the shoulder; and (c) positioning a conformal support pad along said strap to contact an injured region of the shoulder.

12. A method as set forth in claim 11 including a wrist support having a fastener region of hook and loop fastener material and comprising the steps of retaining said support to the wrist and further retaining said fastener region to said belt or said strap.

13. A method for treating an injured shoulder comprising:

(a) securing an elastic belt about the torso of a convalescent to establish the length and tension of said belt about the torso, wherein said belt includes a plurality of regions of mating first and second fasteners secured to front and back surfaces of said belt;

(b) training first and second elastic straps, wherein each of said first and second straps includes a plurality of regions of mating first and second fasteners secured to front and back surfaces of said first and second straps, over first and second shoulders of a convalescent to mate with selected ones of the fastener regions at said belt to establish the tension of each of said first and second straps about the shoulders; and (c) positioning a conformal support pad along each of said first and second straps to contact an injured region of each shoulder.

* * * * *